(12) United States Patent
Lenkei et al.

(10) Patent No.: US 11,617,560 B2
(45) Date of Patent: Apr. 4, 2023

(54) METHOD FOR IMAGING A SAMPLE WITH BLOOD AND ASSOCIATED DEVICES

(71) Applicants: INSERM (INSTITUT NATIONAL DE LA SANTE ET DE LA RECHERCHE MEDICALE), Paris (FR); CENTRE NATIONAL DE LA RECHERCHE SCIENTIFIQUE, Paris (FR);
(Continued)

(72) Inventors: Zsolt Lenkei, Paris (FR); Mathieu Pernot, Paris (FR); Mickael Tanter, Paris (FR); Thomas Deffieux, Paris (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE, Paris (FR); ECOLE SUPERIEURE DE PHYSIQUE ET DE CHIME INDUSTRIELLES DE LA VILLE DE PARIS, Paris (FR); UNIVERSITÉ PARIS CITÉ, Paris (FR); SORBONNE UNIVERSITÉ, Paris (FR)

( * ) Notice: Subject to any disclaimer, the term of this patent is extended or adjusted under 35 U.S.C. 154(b) by 290 days.

(21) Appl. No.: 16/330,948

(22) PCT Filed: Sep. 15, 2017

(86) PCT No.: PCT/EP2017/073271
§ 371 (c)(1),
(2) Date: Mar. 6, 2019

(87) PCT Pub. No.: WO2018/050817
PCT Pub. Date: Mar. 22, 2018

(65) Prior Publication Data
US 2019/0247011 A1    Aug. 15, 2019

(30) Foreign Application Priority Data
Sep. 16, 2016   (EP) .................................. 16306185

(51) Int. Cl.
*A61B 8/06* (2006.01)
*A61B 8/00* (2006.01)
(Continued)

(52) U.S. Cl.
CPC .............. *A61B 8/06* (2013.01); *A61B 8/0891* (2013.01); *A61B 8/4494* (2013.01); *A61B 8/488* (2013.01);
(Continued)

(58) Field of Classification Search
CPC ..... A61B 8/0891; A61B 8/4494; A61B 8/488; A61B 8/5207; A61B 8/085; A61B 8/06;
(Continued)

(56) References Cited

U.S. PATENT DOCUMENTS 6,318,179 B1 * 11/2001 Hamilton ................. A61B 8/06
                                                              600/454
9,610,061 B2 *  4/2017 Ebbini .................... A61B 8/085
(Continued)

OTHER PUBLICATIONS

Bercoff et al: "Ultrafast compound doppler imaging: providing full blood flow characterization", IEEE Transactions on Ultrasonics Ferroelectrics and Frequency Control, IEEE, US, vol. 58, No. 1, pp. 134-147, Jan. 1, 2011.
(Continued)

*Primary Examiner* — Oommen Jacob
*Assistant Examiner* — Nyrobi Celestine
(74) *Attorney, Agent, or Firm* — WCF IP (57) ABSTRACT

The present invention aims at improving the Doppler imaging of a biological sample comprising blood. For this, it is
(Continued)

proposed a method for imaging a biological sample (10), the sample (10) comprising blood (14) comprising diffusors and solid tissue (16), the method comprising obtaining observation, each observation being characterized by a different point spread function associating a signal to each location of the region of interest, the signal comprising a first contribution representative of the diffusors of blood vessels within the location, a second contribution representative of the tissue diffusors and a third contribution representative of blood signal associated to blood diffusors outside of the location, and estimating, for each location, the blood flow by using a statistical analysis.

15 Claims, 7 Drawing Sheets

(71) Applicants: ECOLE SUPERIEURE DE PHYSIQUE ET DE CHIMIE INDUSTRIELLES DE LA VILLE DE PARIS, Paris (FR); UNIVERSITE PARIS DIDEROT—PARIS 7, Paris (FR); SORBONNE UNIVERSITE, Paris (FR)

(51) Int. Cl.
*A61B 8/08* (2006.01)
*G01S 15/89* (2006.01)
*G01S 7/52* (2006.01)
*A61B 8/14* (2006.01)

(52) U.S. Cl.
CPC ........ *A61B 8/5207* (2013.01); *G01S 7/52077* (2013.01); *G01S 15/8925* (2013.01); *G01S 15/8981* (2013.01); *A61B 8/085* (2013.01); *A61B 8/14* (2013.01); *A61B 8/145* (2013.01); *G01S 15/8927* (2013.01)

(58) Field of Classification Search
CPC ............. G01S 7/52077; G01S 15/8925; G01S 15/8981; G01S 15/8927
See application file for complete search history.

(56) References Cited

U.S. PATENT DOCUMENTS

| | | |
|---|---|---|
| 2005/0043622 A1* | 2/2005 | Jensen ................ G01S 15/8915 600/449 |
| 2006/0042389 A1 | 3/2006 | Sato et al. |
| 2007/0047788 A1* | 3/2007 | Slablaugh ................ G06T 7/12 382/128 |
| 2009/0304246 A1* | 12/2009 | Walker ................ G01S 7/52034 382/128 |
| 2011/0319766 A1 | 12/2011 | Tsuruno |
| 2013/0094729 A1 | 4/2013 | Mauldin, Jr. et al. |
| 2014/0031689 A1* | 1/2014 | Kang ..................... G06T 5/003 600/443 |
| 2014/0081144 A1* | 3/2014 | Moehring .............. A61B 5/725 600/454 |
| 2015/0224346 A1 | 8/2015 | Coviello et al. |
| 2015/0366540 A1* | 12/2015 | Sato ....................... A61B 8/461 600/453 |
| 2016/0013015 A1* | 1/2016 | Potocek .................. H01J 37/28 250/307 |
| 2016/0157828 A1* | 6/2016 | Sumi .................... G01N 29/262 702/189 |
| 2016/0206285 A1* | 7/2016 | Christiansen ....... G01S 15/8925 |
| 2018/0088220 A1* | 3/2018 | Flynn .................... G01S 7/5202 |
| 2019/0046161 A1* | 2/2019 | Mansour ............. G01S 15/8984 |

OTHER PUBLICATIONS

Charlie et al: "4D microvascular imaging based on ultrafast Doppler tomography", Neuroimage, Elsevier, Amsterdam, NL, vol. 127, pp. 472-483, Nov. 10, 2015.

Mace et al: "High sensitivity brain angiography using Ultrafast Doppler", Ultrasonics Symposium (IUS), 2010 IEEE, IEEE, pp. 1194-1197.

Mace et al: "Functional ultrasound imaging of the brain: theory and basic principles", IEEE Transactions on Ultrasonics, Ferroelectics and Frequency Control, IEEE, US, vol. 60, No. 3, pp. 492-506, Mar. 1, 2013.

Charlie et al: "Spatiotemporal Clutter Filtering of Ultrafast Ultrasound Data Highly Increases Doppler and Ultrasound Sensitivity", IEEE Transactions on Medical Imaging, IEEE Service Center, Piscataway, NJ, US, vol. 34, No. 11, pp. 2271-2285, Nov. 1, 2015.

* cited by examiner

METHOD FOR IMAGING A SAMPLE WITH BLOOD AND ASSOCIATED DEVICES

TECHNICAL FIELD OF THE INVENTION

The present invention concerns a method for imaging a biological sample, the sample comprising blood comprising diffusors and solid tissue. The present invention also relates to an associated imaging device, an associated computer product program and an associated computer readable medium.

BACKGROUND OF THE INVENTION

The present invention relates to the domain of Doppler imaging.

Doppler imaging is notably used for imaging brain as explained in the article by Emilie Mace et al., entitled "*Functional Ultrasound Imaging of the Brain: Theory and Basic Principles*" which was published in IEEE Transactions on Ultrasonics, Ferroelectrics, and Frequency Control, volume 60, number 3, published in March 2013.

In this article, it is notably explained that when an ultrasonic pulse is passing through a blood vessel, a small part of the energy is backscattered by red blood cells and the probe can record these echoes. The principle of Doppler ultrasound imaging is to detect the motion of red blood cells by repeating such pulsed emissions and studying the temporal variations of the successive backscattered signals.

The signal is recorded for each pixel of the image. After the acquisition, a clutter filter (high-pass filter) is applied on the recorded signal to reject the tissue signal. A filtered signal (composed of the blood signal and a noise) is obtained. Two parameters are commonly extracted and displayed from the filtered signal: the axial blood velocity at each pixel, which gives a color Doppler image or the mean intensity of the Doppler signal at each pixel, which gives a power Doppler image.

Historically, the power Doppler mode was developed after the color Doppler mode in an effort to better detect small blood vessels. Indeed, the extraction of blood velocity is very sensitive to noise, even though many different estimators have been tested. Moreover, color Doppler is also sensitive to aliasing, which is a major issue in clinics because an aliased signal leads to a wrong estimation of the flow direction. In comparison, it was shown that the estimation of the signal intensity is more robust to noise and relatively insensitive to aliasing.

Therefore, power Doppler is more suited for certain applications and, in particular, to identifying small vessels. Power Doppler gives no information on the blood velocity but it is associated with another relevant hemodynamic parameter: the volume of blood within the pixel. In conditions of constant hematocrit density aggregation conditions and shear rates, power Doppler is, in first approximation, proportional to the partial volume of blood in the voxel.

However, if the flow is sufficiently slow such that the blood signal is attenuated by the wall filter, it may be more difficult to differentiate blood flow from noise. For that purpose, different strategies have been proposed:

In document WO 2009/158399 A1, the use of ultrafast imaging with compounded plane waves is proposed to dramatically increase the signal-to-noise ratio of the power Doppler image thanks to the high number of acquired images as was demonstrated in a article by E. Mace et al., entitled "*Functional ultrasound imaging of the brain*," Nature methods, volume 8, issue 8, pages 662-664, 2011.

Similar disclosures are known from the article by Jérémy BERCOFF et al. entitled «*Ultrafast Compound Doppler Imaging Providing Full Blood Flow Characterization*», the article from Charlie DEMENE et al. entitled «*4D microvascular imaging based on ultrafast Doppler tomography*», articles by E. Mace et al., entitled respectively «*High sensitivity brain angiography using Ultrafast Doppler*» and «*Functional Ultrasound Imaging of the Brain: Theory and Basic Principles*» and another article from Charlie DEMENE et al. entitled «*Spatiotemporal Clutter Filtering of Ultrafast Ultrasound Data Highly Increases Doppler and fUltrasound Sensitivity*». It is known from document WO 2014/193945 A1 a processing based on the covariance of neighbor receive channels to further reduce thermal noise in the power Doppler image as described in an article by Y. L. Li and J. J. Dahl, entitled "*Coherent flow power doppler (CFPD): flow detection using spatial coherence beamforming*" in IEEE Transactions on Ultrasonics, Ferroelectrics, and Frequency Control, volume 62, number 6, pages 1022-1035, June 2015.

In document WO 2016046506 A1, a new ultrafast sequence is proposed which also largely improve the signal to noise ratio of the power Doppler image compared to a standard ultrafast imaging sequence as demonstrated in an article by E. Tiran et al., entitled "*Multiplane wave imaging increases signal-to-noise ratio in ultrafast ultrasound imaging*" Physics in Medicine and Biology, vol. 60, iss. 21, pp. 8549-8566, 2015.

In addition to noise, slowly moving tissue or reverberation clutter that can pass through the wall filter degrades the power Doppler image since it appears similar to slowly moving blood. For that regard, a new spatiotemporal clutter filter was proposed in the article C. Demene et al., "*Spatiotemporal clutter filtering of ultrafast ultrasound data highly increases Doppler and fUltrasound sensitivity*" IEEE Transactions on Medical Imaging, volume 1, issue 1, 2015 which dramatically improves the separation between slow blood flow and tissue signal, resulting in higher quality Doppler images.

Another method to increase the signal-to-noise ratio of power Doppler images, relies on the use of ultrasound contrast agents that are injected into the blood flow (article by R. Williams et al. whose title is "*Dynamic microbubble contrast-enhanced US to measure tumor response to targeted therapy: a proposed clinical protocol with results from renal cell carcinoma patients receiving antiangiogenic therapy*" in Radiology 2011). To improve the resolution of Doppler images, document WO 2012/080614 A1 proposes to use contrast agents which can precisely be tracked individually in space and time and detect the presence of a blood vessel at a very precise location.

SUMMARY OF THE INVENTION

The invention aims at improving the Doppler imaging of a biological sample comprising blood.

More precisely, the present invention aims to improve the resolution and the contrast of Doppler images without necessarily relying on contrast agents. The invention proposes to reduce the presence of blood signal clutter, that is the undesired blood flow component originating from outside of the location of interest and spread by an imperfect imaging point spread function such as sidelobes.

The method allows to extract the slow time profile of the blood signal from a specific location of interest corresponding to the signal commonly observed within a set of different observations and originating from the overlapped volumes of their partially decorrelated point spread functions. This extraction is possible since blood signals originating from distinct locations appear highly decorrelated in the slow time due to the randomly flowing diffusors, as shown in C. Demene et al in FIG. 2. As such the non-overlapping volumes of the partially decorrelated point spread functions have distinct uncorrelated slow time profiles contrary to the component originating from the overlapping volume. The method is thus of particular interest when the transducer geometry naturally imposes highly decorrelated point spread functions between observations such as sparse arrays, Vernier arrays or row-column arrays.

To this end, the present invention concerns a method for imaging a biological sample, the sample comprising blood diffusors and solid tissue diffusors, the method comprising an imaging step comprising the following operations: an emitting operation in which unfocused ultrasound waves in the region of interest are emitted during a time interval, the ratio of the number of unfocused ultrasound waves over the time interval being superior or equal to 100 unfocused ultrasound waves per second, a collecting operation in which retroreflected waves from the diffusors of the given region of interest are collected, and an image formation operation in which different observations of a region of interest are generated based on the collected retroreflected waves, each observation being characterized by a different point spread function associating a signal to each location of the region of interest, the signal comprising a first contribution representative of the diffusors of blood vessels within the location, a second contribution representative of the tissue diffusors and a third contribution representative of blood signal associated to blood diffusors outside of the location, the second and third contribution being undesired. The imaging step is iterated M times to obtain observation sets of M temporal realizations of the region of interest, M being superior or equal to 10. The method further comprises a filtering step for reducing the second contribution of each of the observation sets, and an estimating step in which, for each location of the region of interest, the blood flow signal is estimated, the estimating step comprising the following operations: applying a statistical analysis on each observation set to discriminate the first contribution and the third contribution, and calculating an estimate of the component of the blood flow signal based on the first contribution.

Such method relies on the spatial decorrelation of blood signal, which implies a low joint variability of the third contribution within the observation sets.

The method enables to discriminate the first contribution, that is the contribution representative of diffusors of blood inside the pixel, from the clutter contribution. More precisely, the method enables to obtain the first contribution without the second contribution coming from the solid tissue and the third contribution coming from blood outside of the location of interest.

The discrimination between the first contribution and the third contribution is enabled by the use of the spatial decorrelation of blood signals originating from distinct locations through the statistical analysis operation based on the joint variability of the observation sets. The statistical analysis can be performed by computing for example the conjugate product, the cross-covariance, or by performing a principal component analysis (PCA) or a singular value decomposition (SVD) or independent component analysis (ICA) or any other mathematical tools based on joint variability analysis.

It is to be noted that the disclosed method is thus very different from calculating a particular Doppler statistical value such as the mean Doppler frequency as proposed in the prior art since calculating a mean Doppler frequency does not enable any discrimination between the first contribution and the third contribution. In such case, the mean Doppler frequency only enable to better obtain the value corresponding to both contributions (the first and the third) without knowing to what extent the third contribution contributes to the measured signal.

It is also to be noted that the step of "applying a statistical analysis on the observations of each set to discriminate the first contribution and the third contribution" is to be understood as a step of "applying a statistical analysis based on the joint variability of the observation sets to discriminate the first contribution and the third contribution".

In other words, the present invention concerns a method for imaging a biological sample, the sample comprising blood diffusors and solid tissue diffusors, the method comprising an imaging step comprising the following operations: an emitting operation in which unfocused ultrasound waves in the region of interest are emitted during a time interval, the ratio of the number of unfocused ultrasound waves over the time interval being superior or equal to 100 unfocused ultrasound waves per second, a collecting operation in which retroreflected waves from the diffusors of the given region of interest are collected, and an image formation operation in which different observations of a region of interest are generated based on the collected retroreflected waves, each observation being characterized by a different and partially spatially decorrelated point spread function associating a signal to each location of the region of interest, the signal comprising a first contribution representative of the diffusors of blood vessels within the location, a second contribution representative of the tissue diffusors and a third contribution representative of blood signal associated to blood diffusors outside of the location, the second and third contribution being undesired. The imaging step is iterated M times to obtain observation sets of M temporal realizations of the region of interest, M being superior or equal to 10. The method further comprises a filtering step for reducing the second contribution of each of the observation sets, and an estimating step in which, for each location of the region of interest, the blood flow signal is estimated, the estimating step comprising the following operations: applying a statistical analysis based on the joint variability of the observation sets to discriminate the first contribution and the third contribution, and calculating an estimate of the component of the blood flow signal based on the first contribution.

As a consequence, thanks to the invention, for the case of a biological sample with blood, the method of the present invention enables to obtain an image with an improved resolution since only the signal corresponding to the overlapping point spread function is recovered.

According to further aspects of the invention which are advantageous but not compulsory, the device might incorporate one or several of the following features, taken in any technically admissible combination:
  the emitting and collecting operations are carried out by using a row-column array of ultrasound transducers.
  the imaging step is carried so that the observations are characterized by partially spatially decorrelated point spread functions.
  the ratio of the number of unfocused ultrasound waves over the time interval is superior or equal to 500 unfocused ultrasound waves per second.
  the number of observations is the same for each set of observations.
  the number of observations is superior or equal to 2.

the number of observations is equal to 2.

the emitting and collecting operations are carried out by using an array of ultrasound transducers, the array of ultrasound transducers being one of a one-dimensional array, a two-dimensional array and a sparse array.

the emitting and collecting operations are carried out by using two orthogonal arrays of ultrasound transducers.

at the operation of applying, the statistical analysis is chosen among a principal component analysis, a singular value decomposition and an independent component analysis.

the operation of applying the statistical analysis comprises estimating the conjugated product between pairs of observations.

the operation of applying the statistical analysis comprises calculating an estimate of the covariance of the observations.

the integer M is superior or equal to 20.

the integer M is superior or equal to 50.

the emitting and collecting operations are carried out by using an array of ultrasound transducers adapted to electronically focus in reception along two preferential directions.

the blood scatterers are acoustic contrast agents.

The specification also relates to an imaging device for imaging a biological sample, the sample comprising blood comprising diffusors and solid tissue, the imaging device comprising an ultrasound imager adapted to carry out an imaging step comprising the following operations: an emitting operation in which unfocused ultrasound waves in the region of interest are emitted during a time interval, the ratio of the number of unfocused ultrasound waves over the time interval being superior or equal to 100 unfocused ultrasound waves per second, a collecting operation in which retroreflected waves from the diffusors of the given region of interest are collected, and an image formation operation in which different observations of a region of interest are generated based on the collected retroreflected waves, each observation being characterized by a different point spread function associating a signal to each location of the region of interest, the signal comprising a first contribution representative of the diffusors of blood vessels within the location, a second contribution representative of the tissue diffusors and a third contribution representative of blood signal associated to blood diffusors outside of the location, the second and third contribution being undesired, the imaging step being iterated M times to obtain observation sets of M temporal realizations of the region of interest, M being superior or equal to 10. The imaging device further comprises a calculator adapted to carry out a filtering step for reducing the second contribution of each of the observation sets, and an estimating step in which, for each location of the region of interest, the blood flow signal is estimated, the estimating step comprising the following operations: applying a statistical analysis on each observation set to discriminate the first contribution and the third contribution, and calculating an estimate of the component of the blood flow signal based on the first contribution.

The specification also concerns a computer program product comprising instructions for carrying out at least the estimating step a method as previously described when said computer program product is executed on a suitable computer device.

The specification also relates to a computer readable medium having encoded thereon a computer program product.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Figure 1:
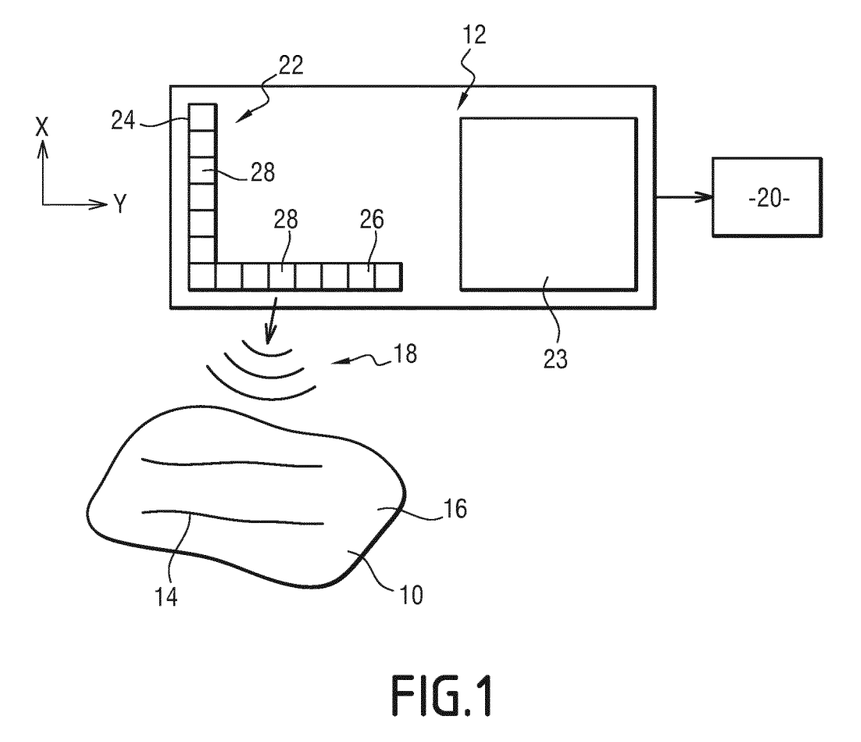
FIG. 1 shows schematically a sample to be imaged and an imaging device for imaging such sample.

A sample 10 to be imaged and an imaging device 12 are illustrated on FIG. 1.

The sample 10 is a biological sample.

By "biological sample", it is meant that the sample 10 originates from a biological being.

For instance, the biological being is a mammal or a human being.

The sample 10 comprises a liquid tissue 14 and a solid tissue 16.

In such context, the liquid tissue 14 is blood and such liquid tissue 14 is represented as two vessels 14.

Each blood vessels 14 comprises diffusors.

By "diffusor", it is meant a particle adapted to diffuse ultrasound waves.

Acoustic contrast agents are specific examples of diffusors. For instance, gaseous bubbles may be considered.

The imaging device 12 is adapted to image the sample 10.

More precisely, the imaging device is adapted to convert the information collected by ultrasound waves 18 into a map 20 of the sample 10.

The imaging device 12 comprises an ultrasound imager 22 and a calculator 23.

Figure 2:
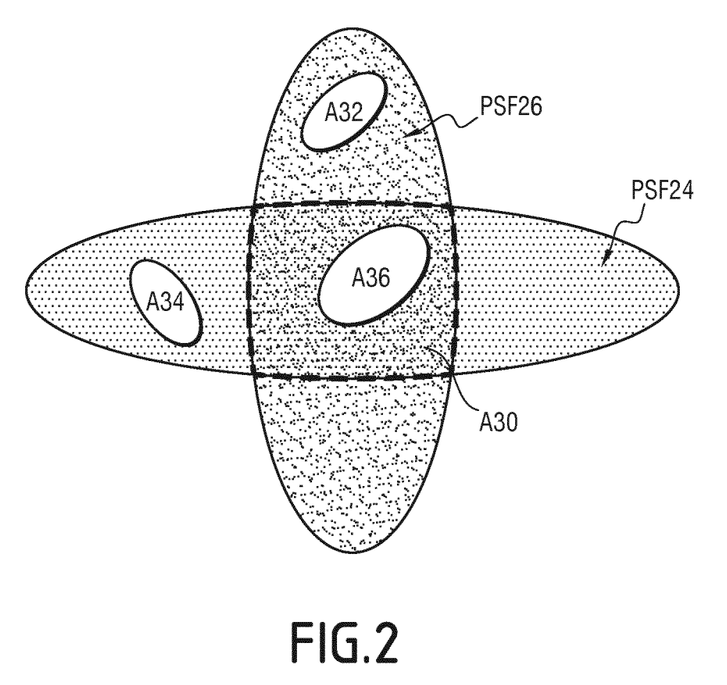
FIG. 2 illustrates a region of interest of the sample illuminated by the imaging device.

The ultrasound imager 22 is adapted to image a region of interest of the sample 10 as schematically illustrated in FIG. 2.

According to the example of FIG. 1, the ultrasound imager 22 comprises a first line of transducers 24 and a second line of transducers 26.

Each line of transducers comprises a plurality of transducers 28.

The first line 24 extends along a first direction named X in the remainder of the specification.

The second line 26 extends along a second direction named Y in the remainder of the specification.

The first direction X and the second direction Y are perpendicular.

Such configuration of ultrasound imager 22 is usually called a row-column array of ultrasound transducers also named by the acronym RCA.

The calculator 23 is adapted to carry out steps of a method for imaging.

Figure 3:
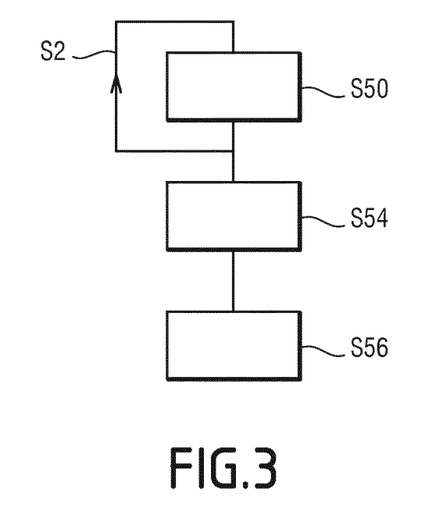
FIG. 3 shows a flowchart illustrating the steps of an example of a method for imaging carried out by the imaging device of FIG. 1.

Operation of the imaging device 12 of FIG. 1 is now described in reference to the flowchart of FIG. 3 which illustrates an example of carrying out a method for imaging the sample 10.

The method comprises an imaging step S50 which is iterated several times as illustrated by an arrow S52, a filtering step S54 and an estimating step S56.

During the imaging step S50, a set of N different observations of the sample 10 are acquired.

Each imaging step S50 comprises several operations: an operation of emitting, an operation of collecting and an operation of image formation.

During the operation of emitting, unfocused ultrasound waves are emitted in a given region of interest of the sample 10.

An unfocused ultrasound wave is a wave for which an aperture is defined.

The aperture has a specific size labeled D.

An ultrasound wave is considered as unfocused if the minimal width $W_{min}$ of the ultrasound beam associated to the ultrasound wave at a depth F is larger than the ratio of the product of the wavelength $\lambda$ of the ultrasound wave by the depth F with the specific size D of the aperture. Such condition may be mathematically expressed as:

$$W_{min} > \lambda * F/D$$

Unfocused waves include plane waves or divergent waves.

The location of interest is approximated by the intersection of the point spread functions of each observation.

In the specific case of FIG. 2, the first point spread function PSF24 corresponding to the first line 24 and the second point spread function PSF26 corresponding to the second line 26 are represented.

The point spread function (PSF) describes the response of an imaging system to a point source or point object. A more general term for the PSF is a system's impulse response, the PSF being the impulse response of a focused optical system. The PSF in many contexts can be thought of as the extended blob in an image that represents an unresolved object.

In the case of FIG. 2, the intersection of both point spread function PSF24 and PSF26 is the region of interest A30.

For the sake of illustration, it is supposed that each point spread function comprise a blood area outside the location of interest A30 and a blood area in the location of interest A30.

More precisely, the first point spread function PSF24 encompasses a first blood area A32, the second point spread function PSF26 encompasses a second blood area A34 and the location of interest A30 encompasses a third blood area A36. The third blood area A36 is common to both point spread function PSF24 and PSF26.

The operation of emitting is carried out at a high frame rate.

A high frame rate corresponds to an emission with a pace superior or equal to 100 Hz.

In other words, the unfocused ultrasound waves are emitted during a time interval and the ratio of the number of unfocused ultrasound waves over the time interval is superior or equal to 100 unfocused ultrasound waves per second.

According to another embodiment, the frame rate corresponds to an emission with a pace superior or equal to 500 Hz.

In other words, the unfocused ultrasound waves are emitted during a time interval and the ratio of the number of unfocused ultrasound waves over the time interval is superior or equal to 500 unfocused ultrasound waves per second.

During the operation of collecting, diffusors belonging to the given location of interest interacts with the emitted unfocused ultrasound waves. Notably, the diffusors emit retroreflected waves.

The retroreflected waves are collected on the array.

During the image formation operation, the set of N observations of the given location of interest are formed with different point spread function using a subset of the emission and reception data based on the collected retroreflected waves.

At the end of the first imaging step, a set of N different observations is thus obtained. Each observation associates to the location of interest a distinct signal according to the point spread function of said observation.

The signal comprises a first contribution representative of the diffusors of blood inside the location of interest and a clutter contribution.

The clutter contribution includes a second contribution and a third contribution.

The second contribution comes from the solid tissue.

The third contribution comes from blood outside of the location of interest.

The second contribution and the third contribution are undesired contribution.

The imaging step is iterated M times so as to obtain N observation sets of M temporal realizations.

The integer M is superior or equal to 50.

At the end of the imaging step, each temporal realization comprises a set of N different observations.

During the filtering step, each observation of the M temporal realizations is filtered with a filter.

The filter is a filter reducing the contribution coming from the solid tissue of the given location of interest in the observation.

In other words, the filter is a filter removing the tissue signal.

According to a first example, the filter is a high pass temporal filter.

According to a second example, the filter is a demodulation filter.

According to a third example, the filter is a singular value decomposition over the [M,P] space, where P represents the image space.

At the end of the filtering step, the second contribution has been greatly reduced so that it can be considered that the undesired clutter signal includes only the third contribution.

During the estimating step, the blood flow component is estimated for each location of the region of interest.

The estimating step comprises an operation of applying a statistical analysis, an operation of calculating and an operation of accumulating.

For each set, the operation of applying consists in applying a statistical analysis on each observations of the set to discriminate the first contribution from the third contribution.

The first contribution indeed corresponds to the blood signal originating within the location of interest which can be approached by the overlapping of the point spread functions of all observations of the set.

In other words, the operation of applying consists in applying a statistical analysis on all the observations to emphasize the common signal to the N observations of each set.

At the operation of applying, a statistical analysis is applied on the observations of each set to extract the first contribution.

According to an example, the statistical analysis is a principal component analysis.

Principal component analysis (PCA) is a statistical procedure that uses an orthogonal transformation to convert a set of observations of possibly correlated variables into a set of values of linearly uncorrelated variables called principal components. The number of principal components is less than or equal to the number of original variables. This transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors are an uncorrelated orthogonal basis set. PCA is sensitive to the relative scaling of the original variables.

For instance, the most important principal components will correspond to the first contribution while the less important principal components will correspond to the third contribution.

According to another example, the statistical analysis is a singular value decomposition.

In linear algebra, the singular value decomposition (SVD) is a factorization of a real or complex matrix. It is the generalization of the eigendecomposition of a positive semi-definite normal matrix (for example, a symmetric matrix with positive eigenvalues) to any m×n matrix via an extension of polar decomposition.

According to another example, the statistical analysis is an independent component analysis.

In signal processing, independent component analysis (ICA) is a computational method for separating a multivariate signal into additive subcomponents. This is done by assuming that the subcomponents are non-Gaussian signals and that they are statistically independent from each other. ICA is a special case of blind source separation. A common example application is the "cocktail party problem" of listening in on one person's speech in a noisy room.

In variant, other statistical analyses are also to be considered. For instance, a Karhunen-Loève transform or a correspondence analysis may be considered.

In each example, the statistical analysis is carried out over the [M,N] space to recover the blood flow signal common in the N observations.

Alternatively or in combination, the statistical analysis comprises estimating the conjugated product between pairs of observations. This enables to realign the phase of the first contribution between pairs of observation and accumulate over the M temporal realizations.

At the end of the operation, it is possible to discriminate between the first contribution and the third contribution.

At the operation of calculating, for each set, an estimate of the component of the blood flow signal is calculated based on the extracted contribution.

For instance, the operation of calculating is carried out by evaluating the energy by summing the square of the recovered blood flow signal over the M temporal realizations.

The effect of the method can be explained by a theoretical calculation.

Assuming that i designates a pixel and that $s1(i)$ corresponds to the blood flow measured in the first blood area A32, $s2(i)$ corresponds to the blood flow measured in the second blood area A34 and $s3(i)$ corresponds to the blood flow measured in the third blood area A36, the operation made in the present method corresponds to an operation of correlation. This mathematically corresponds to:

$$P = \Sigma_i (s1(i)+s3(i))^*(s2(i)+s3(i))$$

In the case of blood, there is no correlation between $s1(i)$, $s2(i)$ and $s3(i)$ since they are uncorrelated signals. This leads to:

$$P = \Sigma_i (s3(t))^2$$

By contrast, with a conventional power Doppler, the same reasoning would lead to:

$$P = 4*\Sigma_i(s3(t))^2 + \Sigma_i(s1(t))^2 + \Sigma_i(s2(t))^2$$

The contribution of $\Sigma_i(s1(t))^2$ and $\Sigma_i(s2(t))^2$ are not present in the present method.

This shows that signal from blood vessels outside of the location of interest approximated by the overlapping point spread function can be reduced with the present method.

In other words, the method enables to eliminate, or at least reduce both the second contribution and the third contribution.

This results in a better quality of the image in terms of resolution and contrast obtained by the method.

The effect of the method can be shown experimentally.

The method enables to obtain better images as will now be illustrated in reference to FIGS. 4 to 13.

Figure 4:
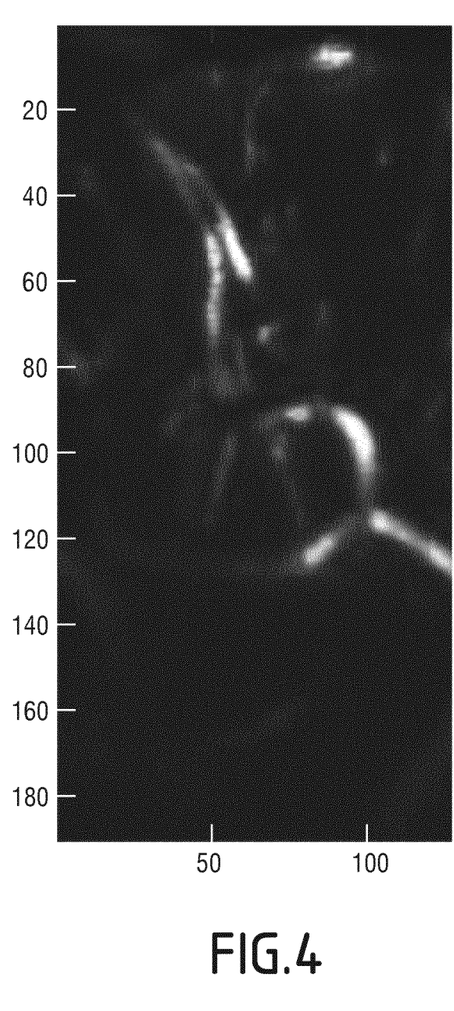
FIG. 4 illustrates a map of a sample obtained by using a power Doppler imaging.
Figure 5:
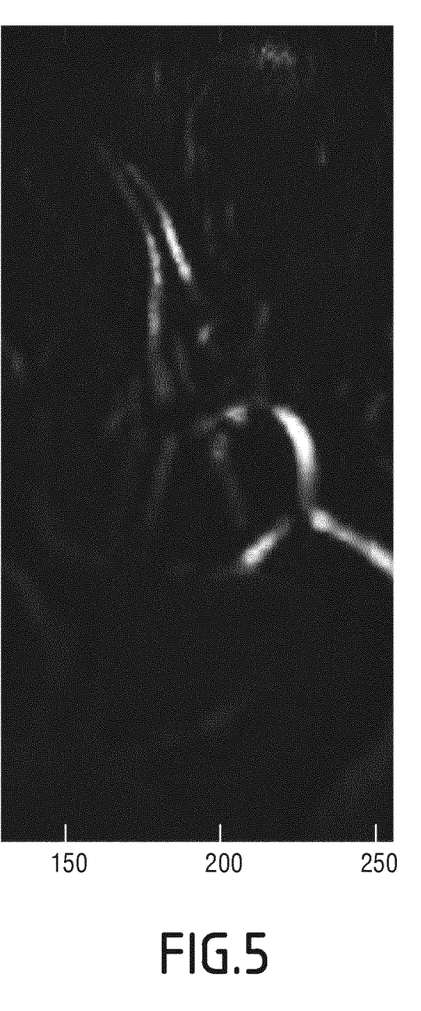
FIG. 5 illustrates a map of a sample obtained by using the method for imaging of FIG. 3, and FIGS. 6 to 13 show experimental results obtained by using the method for imaging of FIG. 3.

For the first experiment, FIG. 4 illustrates a map of a sample obtained by using a power Doppler imaging according to the prior art while FIG. 5 illustrates a map of a sample obtained by using the imaging device 12.

When comparing the map of FIGS. 4 and 5, it appears that more blood vessels are apparent on FIG. 5. This illustrates the fact that the method enables to give access to smaller blood vessels. This means that the spatial resolution of the imaging device 12.

In addition, even for the larger blood vessels which already appear on the map of FIG. 4, the resolution is also improved, the outlines of these blood vessels being more precisely defined in FIG. 5.

Figure 6:
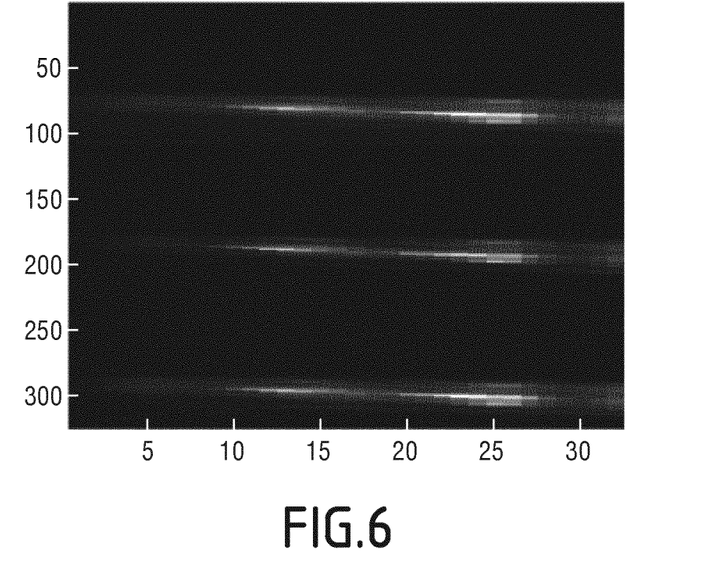
Figure 7:
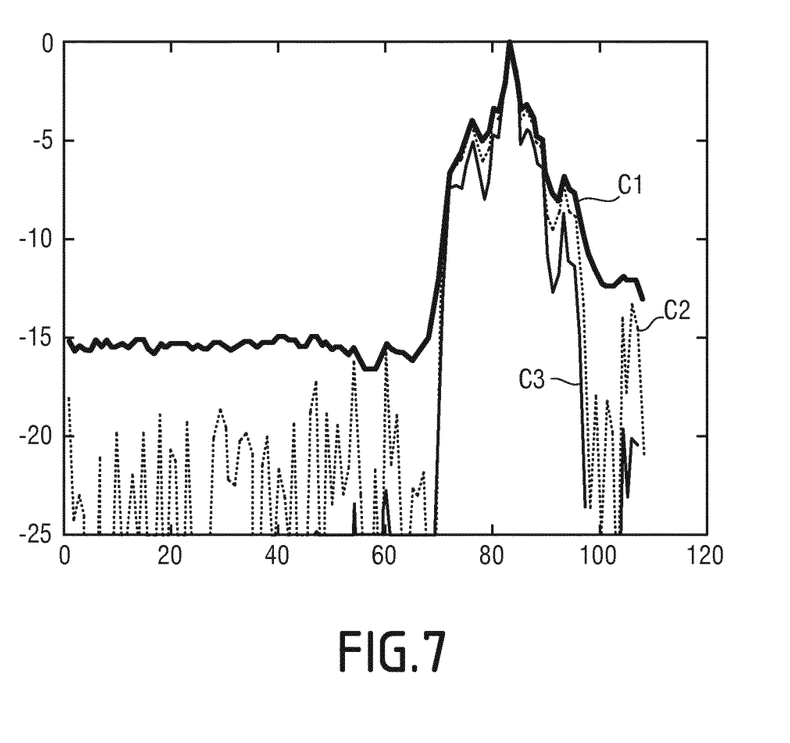

For a second experiment, FIGS. 6 and 7 illustrate the results obtained by imaging the same object (comprising blood) which substantially corresponds to a line extending along a direction of extension.

FIG. 6 illustrates the images obtained by three methods with from top to bottom on FIG. 6 a first method, a second method and a third method. The first method is a conventional power Doppler imaging. The second method is a method according to the invention by using correlations (for the statistical analysis) and the third method is a method according to the invention by using singular value decomposition (for the statistical analysis). In each method, the ultrasound probe is a two-dimensional array of transducers comprising 1024 transducers.

As the images of FIG. 6 are difficult to compare on an eye basis, it is proposed to evaluate the evolution of the intensity along a direction perpendicular to the direction of extension. This evolution is represented in a logarithmic scale on FIG. 7.

Curve C1 corresponds to the first method, curve C2 corresponds to the second method and curve C3 to the third method. It appears that the signal to noise ratio is greatly increased for the curves C2 and C3 compared to curve C1.

Figure 8:
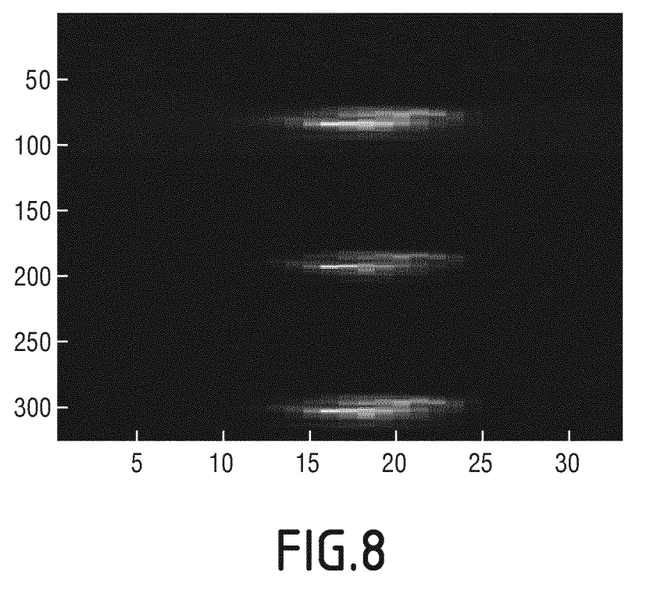
Figure 9:
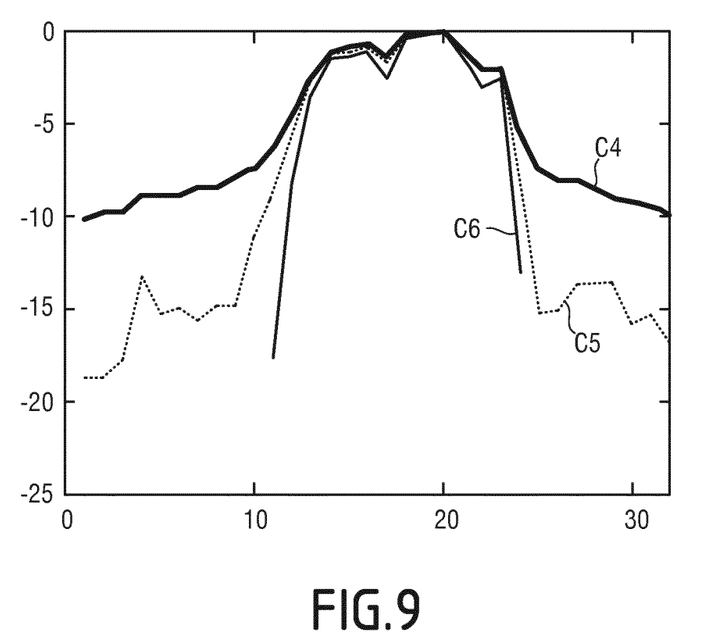

For a third experiment, FIGS. 8 and 9 illustrate the results obtained by imaging another same object (comprising blood) which substantially corresponds to a line extending along a direction of extension.

FIG. 8 illustrates the images obtained by three methods with from top to bottom on FIG. 8 the first method, the second method and the third method.

The images of FIG. 8 clearly show that the object has a better resolution with the second and the third methods.

This is confirmed the evolution of the intensity along a direction perpendicular to the direction of extension. Such evolution is represented in a logarithmic scale on FIG. 9.

Curve C4 corresponds to the first method, curve C5 corresponds to the second method and curve C6 to the third method. It appears that the signal to noise ratio is greatly increased for the curves C5 and C6 compared to curve C4.

So as to emphasize the improvement of the proposed method, further experiments have been carried out with handicaps.

Figure 10:
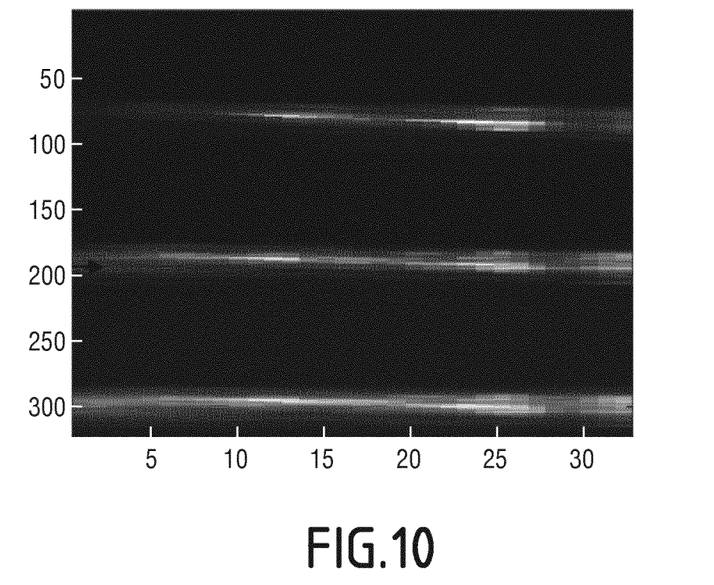
Figure 11:
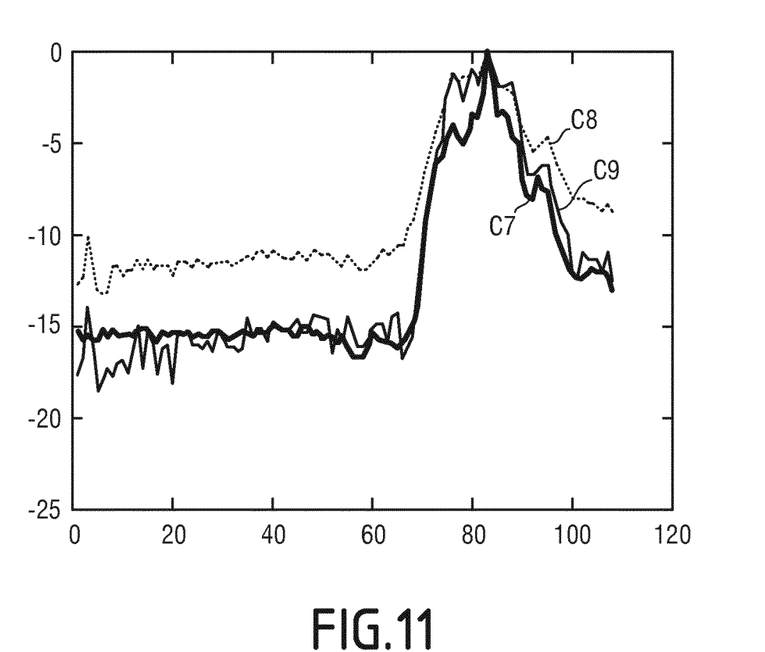

For a fourth experiment, FIGS. 10 and 11 illustrate the results obtained by imaging the same object which substantially corresponds to a line extending along a direction of extension. The object is the same as for the second experiment.

FIG. 10 illustrates the images obtained by three methods with from top to bottom on FIG. 10 the first method, a fourth method and a fifth method. As a reminder, the first method is a conventional power Doppler imaging with a two-dimensional array of transducers comprising 1024 transducers. The fourth method is a method according to the invention by using correlations (for the statistical analysis) in which a row-column array of ultrasound transducers comprising only 64 transducers is used. The fifth method is a conventional power Doppler imaging in which a row-column array of ultrasound transducers comprising only 64 transducers is used.

As expected, the images obtained with the fifth method are degraded by comparison with the first method. The visual observation also shows that the first method and the fourth method seem to be slightly equivalent.

This is confirmed the evolution of the intensity along a direction perpendicular to the direction of extension. Such evolution is represented in a logarithmic scale on FIG. 11.

Curve C7 corresponds to the first method, curve C8 corresponds to the fourth method and curve C9 to the fifth method. It appears that the signal to noise ratio is greatly increased for the curves C7 and C9 compared to curve C8.

This shows that the present invention is able to obtain the same resolution with only 64 transducers compared to a conventional power Doppler imaging with 1024 pixels.

This shows that scientists which are now equipped with only two arrays of 32 transducers could benefit from the resolution of 32*32=1024 transducers provided with conventional power Doppler imaging by modifying the calculator commanding their two arrays of 32 transducers.

Even better, in some cases, such as the case of the object of the third experiment, these scientists could even benefit from a better resolution than the resolution of 32*32=1024 transducers provided with conventional power Doppler imaging.

Figure 12:
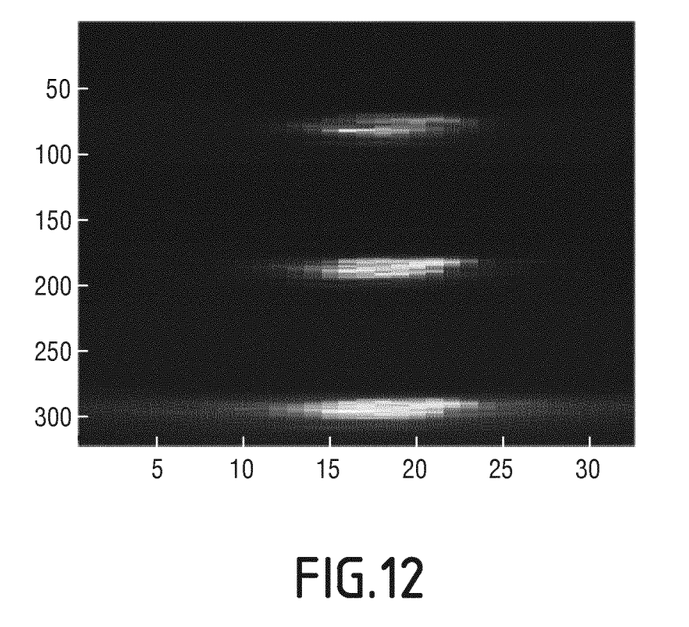
Figure 13:
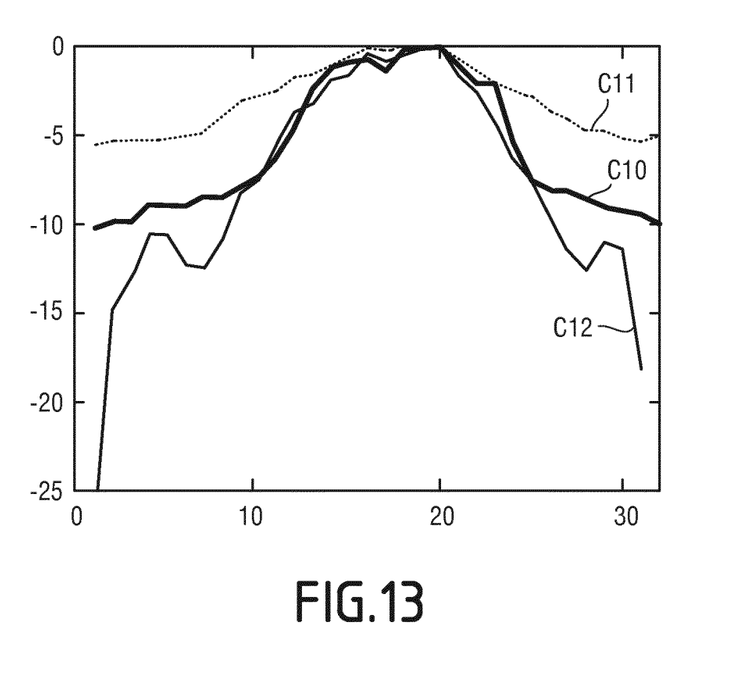

This is illustrated by the fifth experiment whose results are shown on FIGS. 12 and 13.

FIG. 12 illustrates the images obtained by three methods with from top to bottom on FIG. 12 the first method, the fourth method and the fifth method.

As expected, the images obtained with the fifth method are degraded by comparison with the first method. The visual observation also shows that, unexpectedly, the fourth method seems to provide a better image quality than the first method and a fortiori the fifth method.

This is confirmed the evolution of the intensity along a direction perpendicular to the direction of extension. Such evolution is represented in a logarithmic scale on FIG. 13.

Curve C10 corresponds to the first method, curve C11 corresponds to the fourth method and curve C12 to the fifth method. It appears that the signal to noise ratio is greatly increased for the curve C12 when compared with curves C10 and C11.

This means that, thanks to the proposed method, a RCA array comprising 64 transducers provide better images than a two-dimensional array of transducers comprising 1024 transducers.

The previous results illustrate that for the case of a biological sample with blood, the method of the present invention enables to obtain an image with an improved resolution.

This results from a smart use of the property of the blood with the creation of partially spatially decorrelated point spread functions.

In other words, the invention relies on the fact that the blood flow is different from one location to another. Only the common contribution to the observation is temporally correlated.

Other embodiments of the present method may be considered.

For instance, the array of ultrasound transducers is any array of ultrasound transducers adapted to electronically focus in reception along two preferential distinct directions.

Such ultrasound transducers comprises a group of elements defining, physically or virtually, at least two linear or curvilinear subarrays, each subarray being adapted to electronically focus in reception along a preferential direction.

Mills cross arrays, row column arrays, crossed electrode arrays or Top-Orthogonal-to-Bottom-Electrode arrays or annular array are specific examples which may constitute such kind of ultrasound transducers.

According to another example, the array of ultrasound transducers is a group of elements defining, physically or virtually, at least two linear or curvilinear subarrays whose elements spacing is inferior to four wavelengths at the emission central frequency along a unique preferential direction or curve.

For instance, the number of emitted unfocused ultrasound waves may vary from one observation to another.

Furthermore, even if the number of emitted unfocused ultrasound waves is the same, the emitted unfocused ultrasound waves may be emitted at different emitting instants provided the observations be carried out in the same spatial span time.

In addition, the number of observations may vary from one temporal realization from another.

The present invention was described previously with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks. Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

The embodiments and alternative embodiments considered here-above can be combined to generate further embodiments of the invention.

The invention claimed is:

1. A method for imaging a biological sample, the sample comprising diffusors of blood vessels and solid tissue, the method comprising:
   an imaging step comprising the following operations:
      an emitting operation in which unfocused ultrasound waves in a region of interest are emitted during a time interval, the ratio of the number of unfocused ultrasound waves over the time interval being superior or equal to 100 unfocused ultrasound waves per second,
      a collecting operation in which retroreflected waves from the diffusors of the region of interest are collected, and
      an image formation operation in which different observations of the region of interest are generated based on the collected retroreflected waves, each observation being characterized by a different and partially spatially decorrelated point spread function associating a blood flow signal to each location of the region of interest, the blood flow signal comprising a first contribution representative of the diffusors of blood vessels within the location, a second contribution representative of tissue diffusors, and a third contribution representative of blood diffusors outside of the location, wherein the second and third contribution are undesired,
   the imaging step being iterated M times to obtain observation sets of M temporal realizations of the region of interest, M being superior or equal to 10,
   a filtering step for reducing the second contribution of each of the observation sets, and
   an estimating step in which, for each location of the region of interest, the blood flow signal is estimated, the estimating step comprising the following operations:
      applying a statistical analysis operation on each observation set to discriminate the first contribution and the third contribution by the use of the spatial decorrelation of blood signals originating from distinct locations through the statistical analysis operation based on the joint variability of the observations of each set, and
      calculating an estimate of a component of the blood flow signal based on the first contribution.

2. The method according to claim 1, wherein the emitting and collecting operations are carried out by using a row-column array of ultrasound transducers.

3. The method according to claim 1, wherein the ratio of the number of unfocused ultrasound waves over the time interval is superior or equal to 500 unfocused ultrasound waves per second.

4. The method according to claim 1, wherein the number of observations is the same for each set of observations.

5. The method according to claim 1, wherein the number of observations is equal to 2.

6. The method according to claim 1, wherein the emitting and collecting operations are carried out by using an array of ultrasound transducers, the array of ultrasound transducers being one of a one-dimensional array, a two-dimensional array, or a sparse array.

7. The method according to claim 1, wherein the emitting and collecting operations are carried out by using two orthogonal arrays of ultrasound transducers.

8. The method according to claim 1, wherein, at the operation of applying, the statistical analysis is chosen among a principal component analysis, a singular value decomposition and an independent component analysis.

9. The method according to claim 1, wherein the operation of applying the statistical analysis comprises estimating the conjugated product between pairs of observations.

10. The method according to claim 1, wherein the operation of applying the statistical analysis comprises calculating an estimate of the covariance of the observations.

11. The method according to claim 1, wherein the integer M is superior or equal to 20.

12. The method according to claim 1, wherein the emitting and collecting operations are carried out by using an array of ultrasound transducers adapted to electronically focus in reception along two preferential directions.

13. The method according to claim 1, wherein the imaging step uses blood scatterers that are acoustic contrast agents.

14. An imaging device for imaging a biological sample, the sample comprising diffusors of blood vessels and solid tissue, the imaging device comprising an ultrasound imager adapted to carry out an imaging step comprising the following operations:
   an emitting operation in which unfocused ultrasound waves in a region of interest are emitted during a time interval, the ratio of the number of unfocused ultrasound waves over the time interval being superior or equal to 100 unfocused ultrasound waves per second,
   a collecting operation in which retroreflected waves from the diffusors of the region of interest are collected, and
   an image formation operation in which different observations of the region of interest are generated based on the collected retroreflected waves, each observation being characterized by a different and partially spatially decorrelated point spread function associating a blood flow signal to each location of the region of interest, the blood flow signal comprising a first contribution representative of the diffusors of blood vessels within the location, a second contribution representative of tissue diffusors, and a third contribution representative of blood diffusors outside of the location, wherein the second and third contribution are undesired, the imaging step being iterated M times to obtain observation sets of M temporal realizations of the region of interest, M being superior or equal to 10, the imaging device further comprising a calculator adapted to carry out:
- a filtering step for reducing the second contribution of each of the observation sets, and
- an estimating step in which, for each location of the region of interest, the blood flow signal is estimated, the estimating step comprising the following operations:
  - applying a statistical analysis operation on each observation set to discriminate the first contribution and the third contribution by the use of the spatial decorrelation of blood signals originating from distinct locations through the statistical analysis operation based on the joint variability of the observations of each set, and
  - calculating an estimate of a component of the blood flow signal based on the first contribution.

15. A non-transitory computer readable medium encoded with instructions executable by a computer for controlling an ultrasound imager to carry out imaging having the following operations:
an emitting operation in which unfocused ultrasound waves in the region of interest are emitted during a time interval, the ratio of the number of unfocused ultrasound waves over the time interval being superior or equal to 100 unfocused ultrasound waves per second, a collecting operation in which retroreflected waves from the diffusors of the given region of interest are collected, and an image formation operation in which different observations of the region of interest are generated based on the collected retroreflected waves, each observation being characterized by a different and partially spatially decorrelated point spread function associating a blood flow signal to each location of the region of interest, the blood flow signal comprising a first contribution representative of the diffusors of blood vessels within the location, a second contribution representative of tissue diffusors, and a third contribution representative of blood diffusors outside of the location, wherein the second and third contribution are undesired, the imaging device further comprising a calculator controlled by the instructions encoded on the nontransitory computer readable medium to carry out:
- a filtering step for reducing the second contribution of each of the observation sets, and
- an estimating step in which, for each location of the region of interest, the blood flow signal is estimated, the estimating step comprising the following operations:
  - applying a statistical analysis operation on each observation set to discriminate the first contribution and the third contribution by the use of the spatial decorrelation of blood signals originating from distinct locations through the statistical analysis operation based on the joint variability of the observations of each set, and
  - calculating an estimate of a component of the blood flow signal based on the first contribution.

* * * * *

UNITED STATES PATENT AND TRADEMARK OFFICE
CERTIFICATE OF CORRECTION

| | |
|---|---|
| PATENT NO. | : 11,617,560 B2 |
| APPLICATION NO. | : 16/330948 |
| DATED | : April 4, 2023 |
| INVENTOR(S) | : Zsolt Lenkei et al. |

It is certified that error appears in the above-identified patent and that said Letters Patent is hereby corrected as shown below:

On the Title Page

Item (71) Please have applicant name changed from:
INSERM (INSTITUT NATIONAL DE LA SANTE ET DE LA RECHER MEDICALE)
To:
INSTITUT NATIONAL DE LA SANTE ET DE LA RECHERCHE MEDICAEL (INSERM)

Signed and Sealed this
Sixteenth Day of July, 2024

Katherine Kelly Vidal
*Director of the United States Patent and Trademark Office*